United States Patent
Kuroda et al.

(10) Patent No.: US 9,625,273 B2
(45) Date of Patent: Apr. 18, 2017

(54) THICKNESS MEASUREMENT APPARATUS AND METHOD THEREOF

(75) Inventors: Hidehiko Kuroda, Yokohama (JP); Yoshihiro Yamashita, Yokohama (JP); Akio Sumita, Yokohama (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 875 days.

(21) Appl. No.: 13/879,153

(22) PCT Filed: Oct. 11, 2011

(86) PCT No.: PCT/JP2011/073345
§ 371 (c)(1),
(2), (4) Date: Apr. 12, 2013

(87) PCT Pub. No.: WO2012/050090
PCT Pub. Date: Apr. 19, 2012

(65) Prior Publication Data
US 2013/0197846 A1    Aug. 1, 2013

(30) Foreign Application Priority Data
Oct. 12, 2010 (JP) .................... 2010-229943

(51) Int. Cl.
*G01C 25/00* (2006.01)
*G01B 17/02* (2006.01)
(Continued)

(52) U.S. Cl.
CPC .......... *G01C 25/005* (2013.01); *G01B 17/02* (2013.01); *G01B 21/042* (2013.01); *G01N 29/07* (2013.01);
(Continued)

(58) Field of Classification Search
CPC .... G01B 21/042; G01B 17/02; G01C 25/005; G01N 2291/044; G01N 2291/106;
(Continued)

(56) References Cited

U.S. PATENT DOCUMENTS 5,864,601 A * 1/1999 Cattorini ................ G01N 23/04
378/54
8,156,784 B2 * 4/2012 DeAngelo .............. G01B 17/02
73/1.82
(Continued)

FOREIGN PATENT DOCUMENTS

JP    6 347249    12/1994
JP    9 264735    10/1997
(Continued)

OTHER PUBLICATIONS

Junji , JP2009156806 A, 2009, English Translated.*
(Continued)

*Primary Examiner* — John Breene
*Assistant Examiner* — Mohammad Islam
(74) *Attorney, Agent, or Firm* — Oblon, McClelland, Maier & Neustadt, L.L.P.

(57) ABSTRACT

A thickness measurement apparatus and method to measure an object to be inspected. The thickness measurement apparatus includes: an ultrasonic wave transmission/reception device that receives/transmits an ultrasonic wave to/from a wall of a pipe to be inspected, covered with a heat insulation material; a support device that supports the ultrasonic wave transmission/reception device from an outer surface of the pipe to be inspected; a thickness calculation device that measures a propagation time of the ultrasonic wave received/transmitted by the ultrasonic wave transmission/reception device, and calculates thickness of the pipe to be inspected; a calibration board with a predetermined thick- (Continued)

ness greater than a thickness of a dead zone of the ultrasonic wave transmission/reception device; and a calibration board adjustment device that moves the calibration board toward and away from a gap between the ultrasonic wave transmission/reception device and the outer surface of the pipe to be inspected.

9 Claims, 5 Drawing Sheets

(51) Int. Cl.
*G01N 29/30* (2006.01)
*G01N 29/07* (2006.01)
*G01B 21/04* (2006.01)

(52) U.S. Cl.
CPC ... *G01N 29/30* (2013.01); *G01N 2291/02854* (2013.01); *G01N 2291/044* (2013.01); *G01N 2291/102* (2013.01); *G01N 2291/2634* (2013.01)

(58) Field of Classification Search
CPC ......... G01N 2291/2634; G01N 29/265; G01N 2291/02854
See application file for complete search history.

(56) References Cited

U.S. PATENT DOCUMENTS

| | | | |
|---|---|---|---|
| 2003/0033881 A1* | 2/2003 | Lam | G01N 29/0609 73/627 |
| 2004/0123666 A1* | 7/2004 | Ao | G01F 1/662 73/644 |
| 2004/0216512 A1* | 11/2004 | Kwun | G01N 29/07 73/1.82 |
| 2006/0288756 A1* | 12/2006 | De Meurechy | G01N 17/006 73/1.01 |
| 2007/0006658 A1* | 1/2007 | Kennedy | G01N 29/265 73/622 |
| 2008/0163700 A1* | 7/2008 | Huang | G01B 17/025 73/861.25 |
| 2009/0217763 A1* | 9/2009 | Yamano | G01N 29/043 73/622 |
| 2009/0301202 A1* | 12/2009 | Bisiaux | G01N 29/041 73/622 |
| 2011/0030479 A1* | 2/2011 | Murai | G01N 29/043 73/632 |
| 2011/0072905 A1* | 3/2011 | Lam | G01N 29/221 73/622 |
| 2011/0132067 A1* | 6/2011 | Deangelo | G01B 17/02 73/1.82 |

FOREIGN PATENT DOCUMENTS

| | | | |
|---|---|---|---|
| JP | 11 142374 | | 5/1999 |
| JP | H11160295 A | * | 6/1999 |
| JP | 11 304777 | | 11/1999 |
| JP | 2007 232528 | | 9/2007 |
| JP | 200915680 A | * | 7/2009 |

OTHER PUBLICATIONS

Lavender, Ultrasonic Testing of Steel Castings, 1976, pp. 1-38.*
IAEA, Ultrasonic Testing of Materials at Level 2, 1988, IAEA.*
Nakahara et al. JP H11160295 A, 1999, English Translated.*
International Search Report Issued Nov. 8, 2011 in PCT/JP11/73345 Filed Oct. 11, 2011.
International Preliminary Report on Patentability issued May 2, 2013 in PCT/JP2011/073345 filed Oct. 11, 2011.
Written Opinion issued Nov. 8, 2011 in PCT/JP2011/073345 filed Oct. 11, 2011.

* cited by examiner

THICKNESS MEASUREMENT APPARATUS AND METHOD THEREOF

TECHNICAL FIELD

The present invention relates to a thickness measurement apparatus and method thereof, which transmit and receive an ultrasonic wave to an object to be inspected, and measure a thickness of the object to be inspected.

BACKGROUND ART

In general, in a plant, each kind of wide variety pipe is complicatedly installed. A thickness measurement technique by using an ultrasonic wave is well known as a technique of measuring thickness of these pipes. For example, a pipe inspection apparatus provided an ultrasonic wave probe with an outer surface of a pipe covered with a heat insulation material is disclosed in a Patent Document 1. In the pipe inspection apparatus, since an inspection device is always attached to the gap between the pipe and the heat insulation material, it is unnecessary to strip the heat insulation material from the pipe. Further, the pipe inspection apparatus can use for inspecting the pipe installed in the plant even in a driving (working) state of the plant.

PRIOR ART DOCUMENTS

Patent Documents

Patent Document 1: Japanese Patent Laid-Open Patent Application No. 11-160295 (JP-A-11-160295)

DESCRIPTION OF INVENTION

Problems to be Solved by Invention

If the inspection device is attached to the position between the pipe and the heat insulation material, it is necessary that a work for stripping the heat insulation material from the pipe before a thickness measurement and covering the pipe with the heat insulation material after the thickness measurement. Meanwhile, in the pipe inspection apparatus disclosed in the Patent Document 1, as the inspection device is always attached to the gap between the pipe and the heat insulation material, the pipe inspection apparatus eliminates works for stripping the heat insulation material from the pipe and covering the pipe with the heat insulation material. Therefore, the pipe inspection apparatus is effective.

However, in case where the inspection device is always attached for the thickness measurement of the pipe, since a region in the heat insulation material becomes high temperature, there is a possibility occurring a heat deterioration of the inspection device. If the heat deterioration of the inspection device occurs, there is an objection that the inspection device can not maintain measurement precision.

In consideration of above circumstance, an object of the present invention is to provide a thickness measurement apparatus and method thereof, which can measure a thickness of an object to be inspected with required sensitively stability and accuracy (precision).

Means for Solving Problem

The above mentioned objects can be achieved according to the present invention by providing, in one aspect, a thickness measurement apparatus comprising: an ultrasonic wave transmission/reception device that receives and transmits an ultrasonic wave to/from a wall of a pipe to be inspected, covered with a heat insulation material; a support device that supports the ultrasonic wave transmission/reception device from an outer surface of the pipe to be inspected; a thickness calculation device that measures a propagation time of the ultrasonic wave received and transmitted by the ultrasonic wave transmission/reception device, and calculates a thickness of the pipe to be inspected; a calibration board of which a thickness is predetermined and more than a thickness of a dead zone of the ultrasonic wave transmission/reception device; and a calibration board adjustment device that moves the calibration board between a gap between the ultrasonic wave transmission/reception device and the outer surface of the pipe to be inspected and the position being different from the gap.

Effect of Invention

The thickness measurement apparatus according to the present invention can measure the thickness of the object to be inspected.

EMBODIMENT FOR CARRYING OUT THE INVENTION

Hereinafter, first, second and third embodiment of a thickness measurement apparatus according to the present invention will be described with reference to the accompanying drawings.

In each embodiment, an indoor-outdoor pipe or buried pipe (underground pipe) installed in a plant is an example of an object to be inspected of the thickness measurement apparatus according to the present invention will be explained. There is a possibility that a flow acceleration corrosion (FAC) or a liquid droplet impingement erosion (LDI) causes a wastage of the pipe in an inner surface of the pipe. Since the wastage of the pipe is a cause of unplanned maintenance and repair work, in the plant, whether the wastage of the pipe is occurred or not is one of important inspection items.

For the sake of increasing (improving) a heat efficiency by suppressing a heat loss, the pipe to be inspected is covered with the heat insulation material. The heat insulation material is, for example, a calcium silicate, a fibrous material such as metal fiber or the like. The heat insulation material is covered with a heat insulation material cover.

It is noted that the object to be inspected includes a plant structure or the like as well as the pipe.

[First Embodiment]

Figure 1:
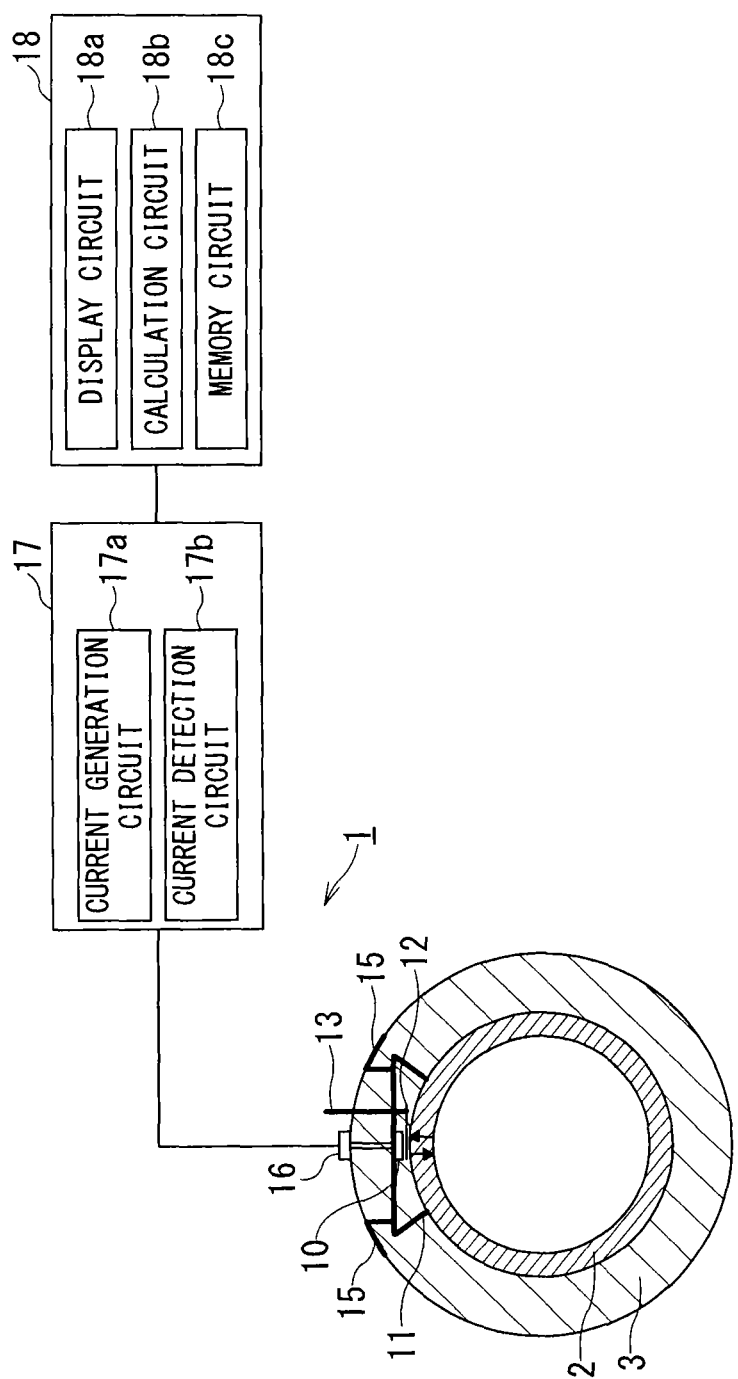
FIG. 1 is a configuration view illustrating first embodiment of the thickness measurement apparatus according to the present invention.

FIG. 1 is a configuration view illustrating first embodiment of the thickness measurement apparatus according to the present invention.

The thickness measurement apparatus 1 includes an electromagnetic ultrasonic wave transmission/reception device 10, a support device 11, a calibration board 12, a calibration board position adjustment device 13, a heat radiation device 15, input-output device (which will be hereinafter referred to as I/O device) 16, a control device 17 and a thickness calculation device 18. In FIG. 1, the pipe to be inspected 2 and heat insulation material 3 respectively are illustrated as cross-section view.

The electromagnetic ultrasonic wave transmission/reception device 10 is an electromagnetic acoustic transducer (EMAT) which is an ultrasonic wave probe of an electromagnet type. The electromagnetic ultrasonic wave transmission/reception device 10 generates an ultrasonic wave by means of a coil and a magnet, casts the ultrasonic wave into the pipe to be inspected 2 and receives a reflection wave reflected from an inner surface of the pipe to be inspected 2. Concretely, in the electromagnetic ultrasonic wave transmission/reception device 10, a high frequency current flowing in the coil thereof induces an eddy current at the pipe surface. By Lorentz force generated from the induced eddy current and a magnetic field, the ultrasonic wave is generated in a pipe wall of the pipe to be inspected 2. Further, in case where the ultrasonic wave goes through the magnetic field in the pipe wall, on the contrary, since the ultrasonic wave induces a current in the coil, the ultrasonic wave is detected.

The electromagnetic ultrasonic wave transmission/reception device 10 does not need a contact catalyst, and therefore prevents from being subjected to influence such as an attachment state and an aging change, of the contact catalyst, the attachment state and the aging change which are a cause of sensitivity change of general ultrasonic wave probe, a surface state of the pipe to be inspected 2 or the like. Thereby, the electromagnetic ultrasonic wave transmission/reception device 10 becomes high stability of the sensitivity. Further, the electromagnetic ultrasonic wave transmission/reception device 10 can receive and transmit the ultrasonic wave of a longitudinal wave or a transverse wave in accordance with an arrangement of the coil and the magnet.

The support device 11 supports the electromagnetic ultrasonic wave transmission/reception device 10 from the pipe outer surface and maintains a gap between the electromagnetic ultrasonic wave transmission/reception device 10 and the pipe outer surface. The support device 11 is configured by a material such as steel which has little influence by high temperature or irradiation.

In case where the heat insulation material 3 is the calcium silicate, the support device 11 is fixed to a cutout portion which is formed in a shape being similar to an outer shape of the support device 11. Even in case where the heat insulation material 3 is the fibrous material, the electromagnetic ultrasonic wave transmission/reception device 10 is magnetically attracted to the pipe to be inspected 2 by an operation of the magnet and thereby fixed to the pipe to be inspected 2. Since the support device 11 does not need to attach to the pipe to be inspected 2 by means of attachment such as adhesion, it is easy for the support device 11 to detachably attach to the pipe to be inspected 2.

The calibration board 12 is a steel of which thickness is predetermined and more than a thickness (length) of a dead zone of the electromagnetic ultrasonic wave transmission/reception device 10. The calibration board 12 is configured by a material such as steel which has little influence by high temperature or irradiation, the material which is similar material as the support device 11. The calibration board 12 is set in the gap between the electromagnetic ultrasonic wave transmission/reception device 10 and the pipe outer surface, and used for calibrating each kind of the set value of the thickness measurement apparatus 1 or a determination method of the reflection wave.

The calibration board position adjustment device 13 is a drive mechanism which moves a position of the calibration board 12 by a mechanical power or a man power. The calibration board position adjustment device 13 moves the calibration board 12 between the gap between the electromagnetic ultrasonic wave transmission/reception device 10 and the pipe outer surface and a position being different from the gap.

The heat radiation device 15 is contacted with an outer surface of the heat insulation material 3 at one end and is contacted with the support device 11 at another end. The heat radiation device 15 is constructed by high thermal conduction material such as copper (Cu), silver (Ag), aluminum (Al), gold (Au) or the like. The heat radiation device 15 irradiates a heat which is thermally conducted from the electromagnetic ultrasonic wave transmission/reception device 10 to the support device 11 to outside of the pipe to be inspected 2.

The I/O device 16 is a connector to connect the electromagnetic ultrasonic wave transmission/reception device 10 to the control device 17. The I/O device 16 is provided on the outer surface of the heat insulation material 3 and connects to the electromagnetic ultrasonic wave transmission/reception device 10. The I/O device 16 is provided on the outer surface of the heat insulation material 3 and configured to easily be possible to detachably attach to the heat insulation material 3.

The control device 17 controls the electromagnetic ultrasonic wave transmission/reception device 10 through the I/O device 16. The control device 17 includes a current generation circuit 17a generating the high frequency current and a current detection circuit 17b detecting the high frequency current. The current generation circuit 17a generates the current of predetermined current value and time width (pulse duration time) with predetermined time interval and transmits the current to the electromagnetic ultrasonic wave transmission/reception device 10. The current detection circuit 17b amplifies the current transmitted from the electromagnetic ultrasonic wave transmission/reception device 10, performs a frequency filtering to the current, and detects the current.

The thickness calculation device 18 measures a propagation time of the reflection wave reflected from the inner surface of the pipe to be inspected 2 and calculates the pipe thickness of the pipe to be inspected 2. The thickness calculation device 18 includes a display circuit 18a, a calculation circuit 18b, a memory circuit 18c.

The display circuit 18a displays a reception waveform of the ultrasonic wave based on a current value detected by the current detection circuit 17b. The display circuit 18a is an analog display such that a cathode-ray tube (CRT) display, on which a measurement signal is scanned in a predetermined sweep time or a digital display on which a calculation signal converted into a digital value displays.

The calculation circuit 18b determines the reflection wave reflected from the inner surface of the pipe to be inspected 2 and measures the propagation time of the reflection wave. Thereby, the calculation circuit 18b calculates the thickness of the pipe to be inspected 2. The calculation circuit 18b is an analog circuit, a digital circuit such as a micro processing Unit (MPU), an application specific integrated circuit (ASIC), a field-programmable gate array (FGPA) or the like, a personal computer or the like. The pipe thickness L can be calculated from expression (1) by using the propagation time $t_L$ of the reflection wave.

[Expression 1]

$$L = \frac{v \cdot t_L}{2} \quad (1)$$

Herein, "v" is sound velocity of the ultrasonic wave.

The memory circuit 18c is constructed by a memory such as SRAM (Static Random Access Memory), DRAM (Dynamic Random Access Memory), other semiconductor memory, a magnetic hard disk or an optical memory medium. The value of the pipe thickness L as a digital data is stored in the memory circuit 18c.

Next, operations of the thickness measurement apparatus 1 as the first embodiment of the thickness measurement apparatus will be described.

The control device 17 sets a frequency and the transmission number per second, of the ultrasonic wave transmitted and received by the electromagnetic ultrasonic wave transmission/reception device 10. The control device 17 sets the frequency of the ultrasonic wave based on a time width of a current value. For example, in case where the ultrasonic wave of which the frequency is 2 MHz is used, the time band of the current value is 0.25 microseconds (μsec). The control device 17 arbitrarily sets the transmission number per second based on a time interval at the time when the pipe thickness L is measured. Incidentally, the control device 17 properly adjusts the current value so as to be possible to receive the reflection wave of the pipe thickness, reflected at the inner surface of the pipe. Based on values described above, the control device 17 transmits the high frequency current through the I/O device 16. Thereby, the ultrasonic wave is transmitted to the electromagnetic ultrasonic wave transmission/reception device 10 which is always attached to the inner portion of the heat insulation material 3.

In vicinity of the outer surface in the pipe wall of the pipe to be inspected 2, the ultrasonic wave is generated and propagated to the pipe wall. A part of the ultrasonic wave propagated from the outer surface is reflected at the inner surface of the pipe wall. In the electromagnetic ultrasonic wave transmission/reception device 10, the ultrasonic wave returned to the outer surface of the pipe wall of the ultrasonic wave reflected at the inner surface of the pipe wall is received as the high frequency current. The high frequency current is transmitted to the control device 17 through the I/O device 16. A part of the ultrasonic wave returned to the outer surface of the pipe wall is again reflected at the outer surface of the pipe wall and thereby becomes a multiple reflection wave which is repeatedly reflected at the pipe wall.

The control device 17 presets a filtering frequency for selecting a frequency, of the ultrasonic wave, the frequency which is preset and detects the high frequency current. Namely, since a reception sensitively can be adjusted based on an amplification degree, the control device 17 adjusts the amplification degree so as to receive the reflection wave representing the pipe thickness. The control device 17 allows the display circuit 18a of the thickness calculation device 18 to display the reception waveform of the ultrasonic wave detected by the control device 17.

Figure 2:
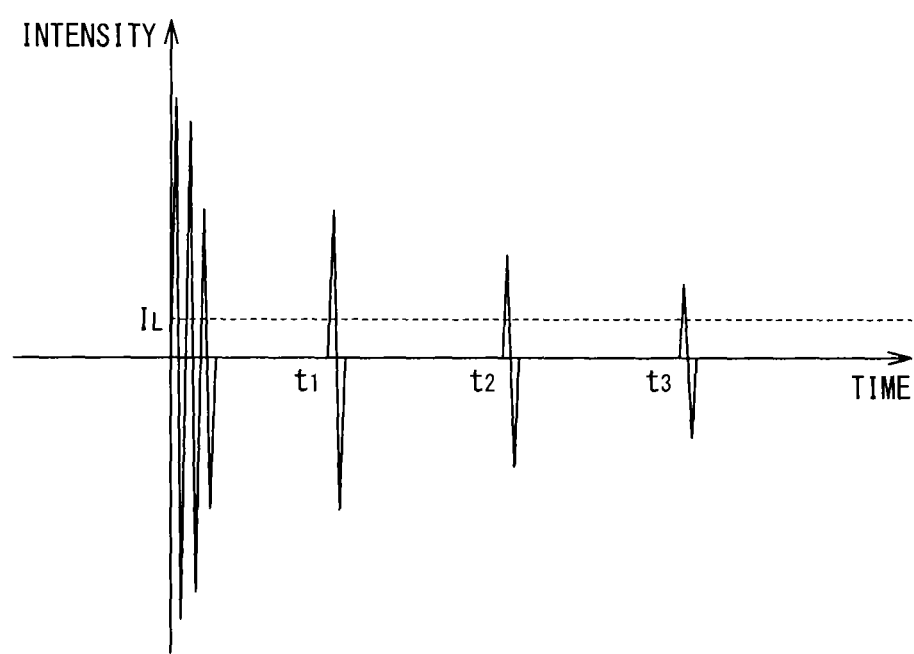
FIG. 2 is an explanation view illustrating an example of reception waveform of an ultrasonic wave displayed in a display circuit.

FIG. 2 is an explanation view illustrating an example of reception waveform of the ultrasonic wave displayed in the display circuit 18a. Incidentally, although only multiple reflection waves at propagation time from $t_1$ to $t_3$ are illustrated in FIG. 2, in reality, multiple reflection waves also occur after the propagation time $t_3$.

The thickness calculation device 18 determines an echo primarily measured in a time or an echo of a maximum intensity as the pipe thickness. Since a maximum value, a minimum value, a set threshold value, or a zero-cross time $t_1$, of the echo becomes the propagation time $t_L$, the thickness calculation device 18 calculates the pipe thickness L by using the expression 1.

The echoes at the propagation time $t_2$ and $t_3$ are respectively multiple reflection waves repeatedly reflected at inner of the pipe wall. Since the thickness calculation device 18 improves an accuracy of determining the propagation time $t_L$ by using expressions (2) to (4), as a result, the pipe thickness L can be calculated with high accuracy.

[Expression 2]

$$t_L = \frac{\sum_{i=1}^{N} t_i}{\sum_{i=1}^{N} i} \quad (2)$$

[Expression 3]

$$t_L = \frac{\sum_{i=1}^{N} \frac{t_i}{i}}{N} \quad (3)$$

[Expression 4]

$$t_L = \frac{\sum_{i=1}^{N} (t_{i+1} - t_i)}{N} \quad (4)$$

The thickness calculation device 18 obtains measurement value of the pipe thickness L with time intervals which is preset for the thickness measurement and stores in the memory circuit 18c in sequence. The thickness calculation device 18 performs a function approximation based on a measurement history of the measurement values in stored the memory circuit 18c and thereby predicts a change of the pipe thickness. The thickness calculation device 18 properly selects a function for performing the function approximation from a power of number, an exponential, a logarithm or a linear. If a database which defines between the pipe thickness L and a relation the measurement history is prepared, the thickness calculation device 18 can predict the pipe thickness L by referring the database.

Next, operations of the calibration board 12 and the calibration board position adjustment device 13, of the thickness measurement apparatus 1 will be described.

In the thickness measurement apparatus 1, as the electromagnetic ultrasonic wave transmission/reception device 10 is always attached to the pipe to be inspected 2 and is used for measuring the pipe thickness over a long term, it is necessary to check measurement accuracy of the electromagnetic ultrasonic wave transmission/reception device 10. Thus, the thickness measurement apparatus 1 calibrates measurement accuracy of the electromagnetic ultrasonic wave transmission/reception device 10 by using the calibration board 12 and the calibration board position adjustment device 13.

The calibration board position adjustment device 13 inserts (sets) in the gap between the electromagnetic ultrasonic wave transmission/reception device 10 and the outer surface of the pipe to be inspected 2. In this case, as is the above-described case with measuring the pipe thickness of the pipe to be inspected 2, the electromagnetic ultrasonic wave transmission/reception device 10 transmits the ultrasonic wave to the calibration board 12 and then receives the reflection wave reflected from the calibration board 12. The thickness calculation device 18 calculates the thickness of the calibration board 12.

The thickness calculation device 18 compares a measurement value of the calibration board 12 and a real thickness of the calibration board 12 which is preliminarily set. When both values obtained by comparing are different from each other, the thickness calculation device 18 calibrates settings such as the set value of the control device 17, the determination method of the reflection wave or the like, for using the thickness measurement of the pipe to be inspected 2.

As described above, even if the electromagnetic ultrasonic wave transmission/reception device 10 is set in the inner portion of the heat insulation material 3 over the long term, by means of the calibration board 12 and the calibration board position adjustment device 13, the thickness measurement apparatus 1 can stably receive the reflection wave representing the pipe thickness.

Incidentally, the check and calibration, of the measurement accuracy may be performed by the user (man) or the thickness measurement apparatus 1 (machine). Especially, when the thickness measurement apparatus 1 operates the calibration board position adjustment device 13, that is, the calibration board position adjustment device 13 automatically adjusts the position of the calibration board 12, the thickness measurement apparatus 1 can check the measurement accuracy even in a state where the plant is driving.

According to the thickness measurement apparatus 1 and method thereof as the first embodiment of the present invention, since the electromagnetic ultrasonic wave transmission/reception device 10 can be always attached to the inner portion of the heat insulation material 3 with high sensitivity stability of the electromagnetic ultrasonic wave transmission/reception device 10, the pipe thickness L can be calculated as needed. Further, since an installation work and a demolition work, of an instrument such as the heat insulation material 3, a scaffold or the like, become unnecessary, the thickness measurement apparatus 1 can efficiently measure the pipe thickness.

Further, by using the calibration board 12 and the calibration board position adjustment device 13, the thickness measurement apparatus 1 can calibrate necessary set value (such as a velocity of the ultrasonic wave, a determination method of the reflection wave or the like) for calculating the pipe thickness L. As a result, even in case where the electromagnetic ultrasonic wave transmission/reception device 10 is installed in the inner portion of the heat insulation material 3 over the long term, the electromagnetic ultrasonic wave transmission/reception device 10 can stably receive the reflection wave representing the pipe thickness.

Furthermore, the heat deterioration of the electromagnetic ultrasonic wave transmission/reception device 10 because of becoming high temperature in the inner portion of the heat insulation material 3 is considered as one of causes which need to calibrate the control device 17 or the thickness calculation device 18. Meanwhile, the heat insulation device 15 can irradiate the heat which is thermally conducted from the electromagnetic ultrasonic wave transmission/reception device 10 to the support device 11 to outside of the pipe to be inspected 2. The thickness measurement apparatus 1 can suppress the number of calibrating the control device 17 or the thickness calculation device 18 because of being high temperature in the inner portion of the heat insulation material 3. Still further, the thickness measurement apparatus 1 can stably receive the reflection wave representing the pipe thickness.

Moreover, since the electromagnetic ultrasonic wave transmission/reception device 10 is always attached to the inner portion of the heat insulation material 3, the thickness measurement apparatus 1 can predict the pipe thickness based on the measurement history of the measurement value of the pipe thickness, continuously measured and realize to measure the pipe thickness over long term.

In addition, the support device 11 integrally supports the electromagnetic ultrasonic wave transmission/reception device 10 and the heat insulation material 3 without attaching to portion contacting between the electromagnetic ultrasonic wave transmission/reception device 10 and the pipe to be inspected 2 by means of strong attachment such as adhesion or the like. Therefore, with respect to the pipe to be inspected 2, the installation and the removal of the thickness measurement apparatus 1 can be easy.

[Second Embodiment]

Figure 3:
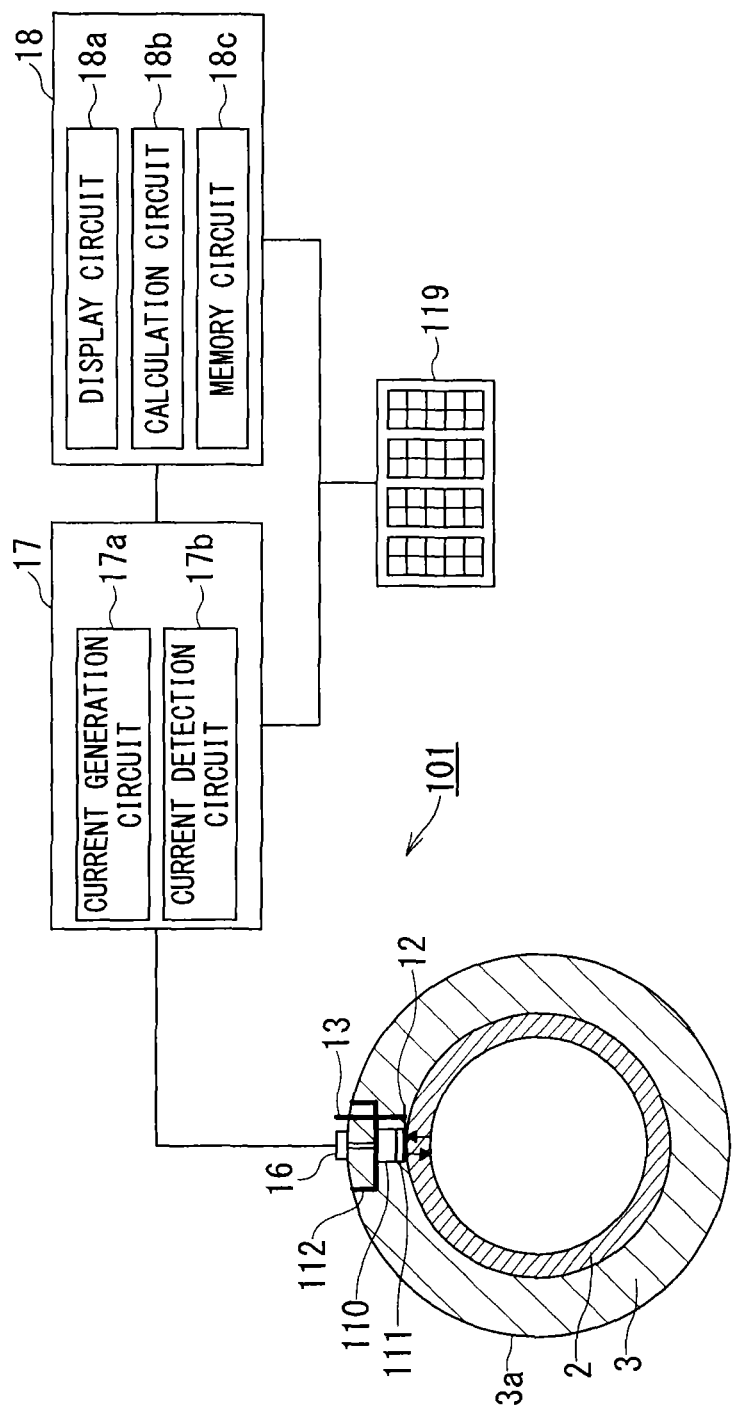
FIG. 3 is a configuration view illustrating second embodiment of the thickness measurement apparatus according to the present invention.

FIG. 3 is a configuration view illustrating second embodiment of the thickness measurement apparatus according to the present invention. In FIG. 3, the pipe to be inspected 2 and heat insulation material 3 respectively are illustrated as cross-section view.

The thickness measurement apparatus 101 includes an ultrasonic wave transmission/reception device 110, an ultrasonic wave transmission device 111, a fixture device 112, the calibration board position adjustment device 13, the I/O device) 16, the control device 17, and the thickness calculation device 18.

The ultrasonic wave transmission/reception device 110 is an ultrasonic wave probe including an ultrasonic wave vibrator which is configured by a piezoelectric element. The ultrasonic wave vibrator is configured by a material such as piezoelectric zirconate titanate (PZT), bismuth titanate, lithium titanate, gallium phosphate ($GaPO_4$) or the like, which has a heat resistance property. The ultrasonic wave transmission/reception device 110 differs from the electromagnetic ultrasonic wave transmission/reception device 10 in view of needing the ultrasonic wave transmission device 111 as the contact catalyst.

The ultrasonic wave transmission device 111 is inserted in a gap between the ultrasonic wave transmission/reception device 110 and the pipe outer surface and transmits the ultrasonic wave. The ultrasonic wave transmission device 111 is configured by soft metal which can transmit the ultrasonic wave, such as nickel (Ni), gold (Au), silver (Ag), copper (Cu), aluminum (Al), or the like. In the ultrasonic wave transmission/reception device 110, since the soft metal is used as the ultrasonic wave transmission device 111, the ultrasonic wave transmission/reception device 110 prevents from being subjected to influence such as the attachment state and the aging change of the contact catalyst, the surface state of the pipe to be inspected 2 or the like. Herein, for the ultrasonic wave probe of which liquid is used as the contact catalyst, the attachment state and the aging change become a cause of sensitivity change. Therefore, the ultrasonic wave transmission/reception device 110 becomes high stability of the sensitivity.

The ultrasonic wave transmission/reception device 110 generates the ultrasonic wave by the vibration of the piezoelectric element applied with the high frequency voltage and propagates the ultrasonic wave from the outer surface of the pipe to be inspected 2 to the inner of the pipe to be inspected 2 thorough the ultrasonic wave transmission device 111. On the contrary, in case where the piezoelectric element receives the vibration of the ultrasonic wave, the piezoelectric element generates the high frequency voltage. Thereby, the ultrasonic wave transmission/reception device 110 detects the ultrasonic wave.

The calibration board 12 is set in the gap between the ultrasonic wave transmission device 111 and the pipe outer surface and is used for the calibrating each kind of setting of the thickness measurement apparatus 101. The calibration board position adjustment device 13 moves the calibration board 12.

The fixture device 112 (the support device) supports the ultrasonic wave transmission/reception device 110 from the outer surface of the pipe. The fixture device 112 is fixed to the heat insulation material 3 and keeps the gap between the ultrasonic wave transmission/reception device 110 and the pipe outer surface. The fixture device 112 fixes the ultrasonic wave transmission device 111 to the gap between the ultrasonic wave transmission/reception device 110 and the pipe outer surface. As is the case with the support device 11, the fixture device 112 is configured by the material such as steel which has little influence by high temperature or irradiation. In case where the heat insulation material 3 is the fibrous material, the fixture device 112 is fixed to the heat insulation material cover 3a of which an intensity is stronger than that of the heat insulation material 3.

The fixture device 112 adjusts the gap between the ultrasonic wave transmission/reception device 110 and the pipe outer surface. Thereby, since a contact character between the ultrasonic wave transmission/reception device 110 and the ultrasonic wave transmission device 111 and a contact character between the ultrasonic wave transmission device 111 and the outer surface of the pipe to be inspected 2 are secured, the ultrasonic wave is effectively transmitted. Since the fixture device 112 integrally fixes the ultrasonic wave transmission/reception device 110 and the heat insulation material 3, it becomes easy to attach the thickness measurement apparatus 101 to the inner portion of the heat insulation material 3 and to remove (detach) the thickness measurement apparatus 101 from the inner portion of the heat insulation material 3.

Further, the fixture device 112 adjusts the gap between the ultrasonic wave transmission device 111 and the outer surface of the pipe, and sets the calibration board 12.

The electromotive force generation device 119 generates an electromotive force based on a heat or a vibration, of the pipe to be inspected 2, or a light radiated from a lighting device (light source) around the electromotive force generation device 119. The electromotive force generation device 119 is configured by a light-electricity conversion element, a heat-electricity conversion element, or the piezoelectric element. The electromotive force generation device 119 generates a part or an entire of the power source being necessary for driving (operating) the control device 17 or the thickness calculation device 18. Namely, in case where the electromotive force generation device 119 generates the electromotive force based on the light radiated from the lighting device which is a light emitting device (LED) used as an indoor lighting device, the electromotive force generation device 119 can generate the electromotive force which is larger than an electromotive force generated by a lighting device other than the LED. In case of using the LED as the light source, the control device 17 or the thickness calculation device 18 can transmit an information by performing a frequency modulation (FM) or an amplitude modulation (AM).

Next, operations of the thickness measurement apparatus 101 as the second embodiment of the thickness measurement apparatus and the measurement method thereof will be described. Incidentally, in regard to operations of the second embodiment of the thickness measurement apparatus and the measurement method thereof, descriptions duplicated with those of the thickness measurement apparatus 1 are omitted (not described).

The control device 17 sets the frequency and the transmission number per second, of the ultrasonic wave. Based on these set values, the control device 17 applies the high frequency current to the ultrasonic wave transmission/reception device 110 through the I/O device 16. The ultrasonic wave is transmitted from the ultrasonic wave transmission/reception device 110 to the inner portion of the pipe to be inspected 2. A part of the ultrasonic wave transmitted to the inner portion of the pipe to be inspected 2 reflects at the inner surface of the pipe wall of the pipe to be inspected 2. A part of the reflection wave reflected at the inner surface of the pipe wall of the pipe to be inspected 2 returns to the outer surface of the pipe wall of the pipe to be inspected 2. The reflection wave returned to the outer surface of the pipe wall of the pipe to be inspected 2 becomes a high frequency voltage in the ultrasonic wave transmission/reception device 110. The high frequency voltage is transmitted to the control device 17 through the I/O device 16. A part of the ultrasonic wave again reflects at the outer surface of the pipe wall and thereby becomes a multi-reflection wave which repeatedly reflects at the pipe wall.

The control device 17 performs the frequency filtering, the amplification and the detection, of the high frequency voltage. The thickness calculation device 18 obtains a reception waveform as the same reception waveform illustrated in FIG. 2 based on the high frequency voltage. The thickness calculation device 18 can calculate pipe thickness L based on the expression (1) described above by using the propagation time $t_L$ calculated by the thickness calculation device 18.

The control device 17 and the thickness calculation device 18 use the electromotive force generated by the electromotive force generation device 119 as a part or an entire of the power source. Thus, even if the ultrasonic wave transmission/reception device 110 is set in the inner portion of the heat insulation material 3 over the long term, the thickness measurement apparatus 101 can stably receive the reflection wave representing the pipe thickness.

According to the thickness measurement apparatus 101 and method thereof as the second embodiment of the present invention, in addition to the effects of the first embodiment according to the present invention, since the electromotive force generated by the electromotive force generation device 119 can be used as the power source, the pipe thickness can be stably measured.

Further, as the fixture device 112 can integrally fix the ultrasonic wave transmission/reception device 110 and the heat insulation material 3, it becomes easy to attach the thickness measurement apparatus 101 to the pipe to be inspected 2 and to remove (detach) the thickness measurement apparatus 101 from the pipe to be inspected 2.

[Third Embodiment]

Figure 4:
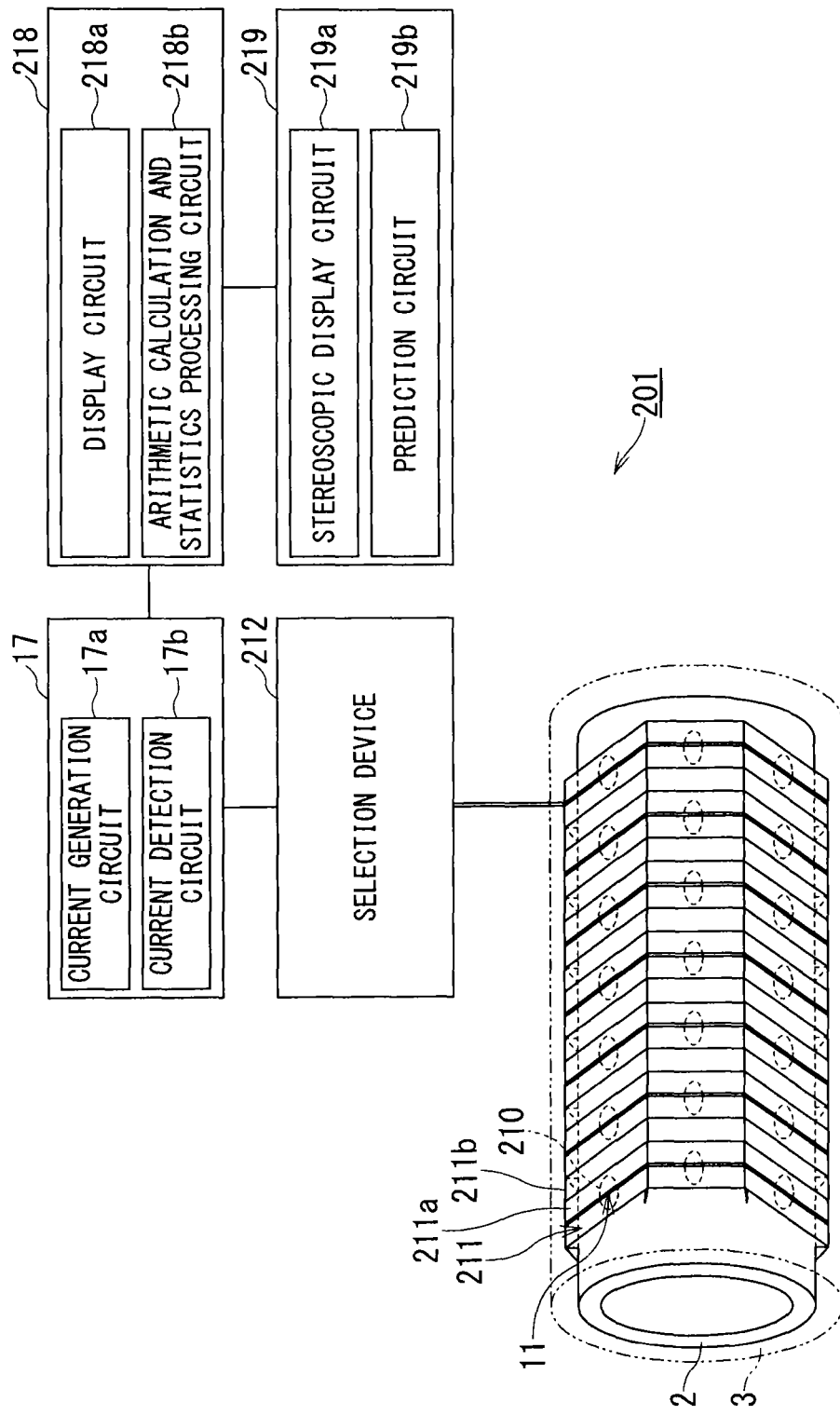
FIG. 4 is a configuration view illustrating third embodiment of the thickness measurement apparatus according to the present invention.

FIG. 4 is a configuration view illustrating third embodiment of the thickness measurement apparatus according to the present invention. Descriptions with regard to components corresponding to the first or the second embodiment of the thickness measurement apparatuses are omitted.

The thickness measurement apparatus 201 includes an electromagnetic ultrasonic wave transmission/reception device 210, a connection device 211, a selection device 212, the control device 17, a statistics calculation device 218 and a thickness distribution calculation device 219. In the thickness measurement apparatus 201 illustrated as the third embodiment of the present invention in FIG. 4, the calibration board 12 and the calibration board position adjustment device 13 is omitted (not illustrated).

The electromagnetic ultrasonic wave transmission/reception devices 210 are a plurality of ultrasonic wave transmission/reception devices. The electromagnetic ultrasonic wave transmission/reception device 210 is as same as the electromagnetic ultrasonic wave transmission/reception device 10 as an ultrasonic wave transmission/reception means of the first embodiment according to the present invention. The number of the electromagnetic ultrasonic wave transmission/reception device 210 is not limited. The electromagnetic ultrasonic wave transmission/reception device 210 of which the number is equal to the number of being required for measuring the thickness of the pipe to be inspected 2 is attached to the measurement portion required for measuring the thickness of the pipe to be inspected 2.

The connection device 211 (the support device) contacts a plurality of the electromagnetic ultrasonic wave transmission/reception device 210 with the pipe to be inspected 2 in a circumferential direction and an axial direction of the pipe to be inspected 2 and supports the electromagnetic ultrasonic wave transmission/reception device 210 from the outer surface of the pipe in the same case as the fixture device 112 being described above. The connection device 211 is fixed to the heat insulation material 3 and keeps the gap between the electromagnetic ultrasonic wave transmission/reception device 210 and the pipe outer surface. Specifically, the connection device 211 is configured by fixtures 211a as the plurality number of fixture means and a thin wire 211b for fixing to the pipe to be inspected 2 in the circumferential direction and the axial direction of the pipe to be inspected 2. The connection device 211 is configured by a material such soft metal or the like, the material which has little influence by high temperature or irradiation.

Figure 5:
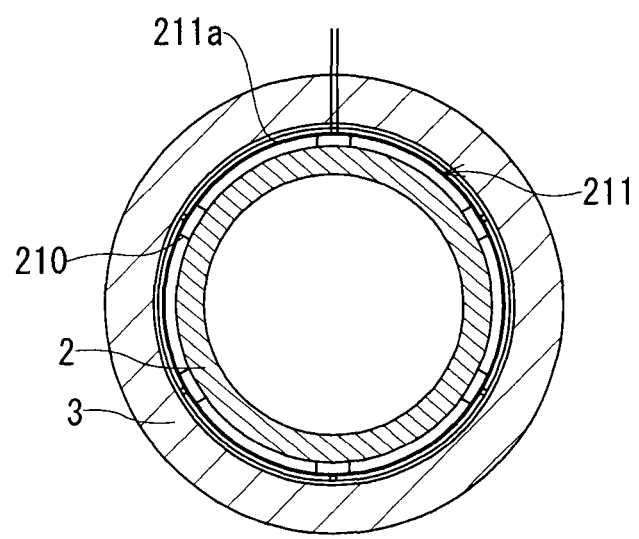
FIG. 5 is a configuration view illustrating another example of third embodiment of the thickness measurement apparatus according to the present invention.

Namely, illustrated as FIG. 5, a shape of cross section of the connection device 211 may be circular shape.

The selection device 212 selects the electromagnetic ultrasonic wave transmission/reception device 210 to be driven (operated) from each of the electromagnetic ultrasonic wave transmission/reception devices 210. The selection device 212 is contacted with the electromagnetic ultrasonic wave transmission/reception device 210 at one end and is configured by a contact circuit (contact point circuit or no contact point circuit) which can individually select from the electromagnetic ultrasonic wave transmission/reception devices 210 by manual operation or mechanical operation. At another end of the selection device 212, the selection device 212 is contacted with the control device 17 and the statistics calculation device 218.

The statistics calculation device 218 measures the propagation time of the multiple-reflection wave received by the electromagnetic ultrasonic wave transmission/reception device 210 selected by the selection device 212 and calculates the pipe thickness of the pipe to be inspected 2 by subjecting the measurement values to the statistics calculation process. The statistics calculation device 218 includes a display circuit 218a and an arithmetic calculation and statistics processing circuit 218b. The arithmetic calculation and statistics processing circuit 218b is an analog circuit, a digital circuit such as MPU, ASIC, FGPA or the like, a personal computer or the like. The arithmetic calculation and statistics processing circuit 218b determines the multiple-reflection wave, measures each propagation time, subjects the measurement value to the statistics calculation process by using above-mentioned Expressions (2) to (4) and following Expression (5), and thereby calculates the pipe thickness L.

[Expression 5]

$$t_L = \sum_{i=1}^{N} \frac{(t_{i+1} + t_i)}{2N} \tag{5}$$

The thickness distribution calculation device 219 measures the propagation time of the multiple-reflection wave received by the electromagnetic ultrasonic wave transmission/reception device 210 arbitrarily selected by the selection device 212 and calculates a thickness distribution of the pipe to be inspected 2. The thickness distribution calculation device 219 includes a stereoscopic display circuit 219a and a prediction circuit 219b. The stereoscopic display circuit 219a correlates the measurement portion measured by each electromagnetic ultrasonic wave transmission/reception device 210 to the pipe thickness at each measurement portion, and stereoscopically displays the measurement portion and the pipe thickness thereof. The stereoscopic display circuit 219a is a two-dimensional display for individually display as three-dimensional display, a projector for actually displaying three-dimensional image or a virtual reality device. The prediction circuit 219b performs an interpolation process by using the measurement value of the pipe thickness or calculates an approximate curve, and thereby estimates pipe thickness at portion other than the measurement portion. The prediction circuit 219b is an analog circuit, a digital circuit such as MPU, ASIC, FGPA or the like, a personal computer or the like.

Next, operations of the thickness measurement apparatus 201 as the third embodiment of the thickness measurement apparatus and the measurement method thereof will be described. Incidentally, in regard to operations of the third embodiment of the thickness measurement apparatus and the measurement method thereof, descriptions duplicated with those of the thickness measurement apparatuses 1 and 101 are omitted (not described).

The control device 17 sets the frequency and the transmission number per second, of the ultrasonic wave. The selection device 212 selects the electromagnetic ultrasonic wave transmission/reception device 210 to be driven (operated). As the same as the operation described in the first embodiment, the statistics calculation device 218 calculates the pipe thickness L based on above-mentioned Expression 1.

By arranging the electromagnetic ultrasonic wave transmission/reception device 210 at required measurement portion, as the thickness measurement apparatus 201 does not need to move the electromagnetic ultrasonic wave transmission/reception device 210, the thickness measurement apparatus 201 can efficiently measure the pipe thickness L at the measurement portion to be measured.

The statistics calculation device 218 sets the intensity threshold value IL illustrated in FIG. 2 and determines the multi-reflection which repeatedly reflects in the pipe wall.

The statistics calculation device 218 statistically improves the accuracy of the propagation time $t_L$ based on the plurality of the propagation time $t_i$ and Expressions (2) to (5). Thereby, the pipe thickness L is calculated with high accuracy and stability based on Expression (1).

After the selection device 212 calculates the pipe thickness L by using the electromagnetic ultrasonic wave transmission/reception device 210 selected by the device 212, the selection device 212 sequentially selects the electromagnetic ultrasonic wave transmission/reception device 210 being placed in the driving state. The statistics calculation device 218 calculates the pipe thickness L at each measurement portion.

Incidentally, when the control device 17 and the statistics calculation device 218 are installed corresponding to the number of the electromagnetic ultrasonic wave transmission/reception device 210, the thickness measurement apparatus 201 allows the selection device 212 to select each of the electromagnetic ultrasonic wave transmission/reception devices 210 and be simultaneously driven. Thereby, the thickness measurement apparatus 201 can collectively measure the thickness at required measurement portion and simultaneously calculate the pipe thickness L.

Each measurement value of each measurement point is stereoscopically displayed by the thickness distribution calculation device 219. Since the thickness distribution calculation device 219 performs the interpolation process by using the measurement value of the pipe thickness or calculates an approximate curve and also estimates the pipe thickness at portion other than the measurement portion, the thickness distribution calculation device 219 can stereoscopically display an object of which the pipe thickness is measured. Since the object of which the pipe thickness is measured is stereoscopically displayed, the operator can speedy understand the pipe thickness at arbitrary measurement portion.

The measurement (monitor) portion may be limited to a curved portion, a throttled (contraction) portion, a portion which has many thickness varieties in accordance with previous measurement history or the like. In this case, in the time when the plant is an operation state or an outage state, the thickness measurement apparatus 201 allows the selection device 212 to select the electromagnetic ultrasonic wave transmission/reception device 210 which transmits to the limited monitor portion, allows the thickness distribution calculation device 219 to stereoscopically display the pipe thickness and can display the history of the measurement value. The operator can speedy understand the pipe thickness at the monitor portion which is limited and the measurement history.

Meanwhile, if there is a portion which has a little thickness variety in consideration of the measurement, the thickness measurement apparatus 201 can decrease the number of the measurement portion by excluding the portion which has a few thickness varieties from the measurement portion.

Herein, as the thickness measurement apparatus 201 includes the electromagnetic ultrasonic wave transmission/reception device 210 and the thickness distribution calculation device 219, the thickness measurement apparatus 201 can achieve following operation and effect.

First, the thickness measurement apparatus 201 arbitrarily selects the electromagnetic ultrasonic wave transmission/reception device 210, for transmission and reception, selected by the selection device 212, and may measure the pipe thickness by a two-probe method. The measurement by the two-probe method can increase the number of the measurement portion of the pipe to be inspected 2. Meanwhile, in case where the number of the measurement point is set, the thickness measurement apparatus 201 can decrease the number of the electromagnetic ultrasonic wave transmission/reception device 210.

Second, the thickness measurement apparatus 201 arbitrary selects the electromagnetic ultrasonic wave transmission/reception device 210 and calculates a flow speed at each measurement portion by using a technique such as a propagation time difference method, a correlation method or the like. By using the flow speed calculation result, the thickness measurement apparatus 201 can set the measurement portion where the flow speed is high as the monitor portion. The reason why the measurement portion where the flow speed is high can be set as the monitor portion is that the pipe thickness variety is subjected to influence of the flow speed in the inner portion of the pipe.

The propagation time difference method is that a flow speed of the ultrasonic wave is calculated, based on a difference between a propagation time of the ultrasonic wave transmitted in a direction from an upstream to a downstream and a propagation time of the ultrasonic wave transmitted in a direction from the downstream to the upstream, by using one pair of the electromagnetic ultrasonic wave transmission/reception device 210. The correlation method is that a flow speed of the ultrasonic wave is calculated based on the distance between an upstream portion and a downstream portion. The upstream portion and the downstream portion are portions where the electromagnetic ultrasonic wave transmission/reception device 210 receives the ultrasonic wave being subjected to a modulation caused by a flow in the pipe. In the correlation method, the distance between the upstream portion and the downstream portion is calculated based on the propagation times at the upstream portion and the downstream portion.

Third, the thickness measurement apparatus 201 allows the electromagnetic ultrasonic wave transmission/reception device 210 to be always attached to the measurement portion and measures the pipe thickness over the long term. Therefore, the thickness measurement apparatus 201 can arbitrarily check the measurement accuracy of each electromagnetic ultrasonic wave transmission/reception device 210. Specifically, the thickness measurement apparatus 201 selects the electromagnetic ultrasonic wave transmission/reception device 210 of which required measurement accuracy is satisfied and measures the pipe thickness as the reference portion. Next, the thickness measurement apparatus 201 selects combination of the electromagnetic ultrasonic wave transmission/reception device 210 which transmits the ultrasonic wave obliquely propagating in the pipe wall to the pipe and can measure the thickness at the reference portion. Then, by using the selected electromagnetic ultrasonic wave transmission/reception device 210, the thickness measurement apparatus 201 measures measure the thickness at the reference portion. In case where the both values are different, the parameter such as the set value of the control device 17, or the like is calibrated. By using the electromagnetic ultrasonic wave transmission/reception device 210 which is calibrated, required measurement accuracy can be satisfied.

The thickness measurement apparatus 201 can check the measurement accuracy by repeatedly performing the calibrating operation with respect to each of the electromagnetic ultrasonic wave transmission/reception devices 210. Therefore, even in case where the electromagnetic ultrasonic wave transmission/reception device 210 is set in the inner portion of the heat insulation material 3 over the long term, the thickness measurement apparatus 201 can stably receive the reflection wave representing the pipe thickness. Incidentally, the thickness measurement apparatus 201 can check the measurement accuracy regardless whether the plant drives or not.

According to the thickness measurement apparatus 201 and the method thereof, in addition to the effects of the first and the second embodiments according to the present invention, since it is not necessary to move one electromagnetic ultrasonic wave transmission/reception device 210, the pipe thickness at the measurement portion to be measured can be measured. Thus, the thickness measurement apparatus 201 and the method thereof can effectively measure the pipe thickness.

Further, in case where the thickness measurement apparatus 201 selects the electromagnetic ultrasonic wave transmission/reception device 210 and subjects the electromagnetic ultrasonic wave transmission/reception device 210 to simultaneously drive, the thickness measurement apparatus 201 can collectively measure the thickness at required measurement portion and simultaneously calculate the pipe thickness.

Furthermore, since the thickness measurement apparatus 201 stereoscopically display calculation result such as the measurement value of the pipe thickness at each measurement portion, estimation value obtained by performing the interpolation process or by calculating based on the approximate curve, or the like, the operator can speedy understand or estimate the pipe thickness.

Although some embodiments of the present invention are described in this specification, these embodiments are merely described as examples and do not intend to limit to the scope of the invention. Various omissions, substitutions, and changes may be made without departing from the spirit and scope of the invention. These embodiments and modifications thereof are included within the sprit and scope of the invention and are included within the scope of the invention as disclosed in the claims and equivalents thereof.

REFERENCE NUMERALS 1, 101, 201 . . . thickness measurement apparatus
2 . . . pipe to be inspected
3 . . . heat insulation material
3a . . . heat insulation material cover
10 . . . electromagnetic ultrasonic wave transmission/reception device
11 . . . support device
12 . . . calibration board
13 . . . calibration board position adjustment device
15 . . . heat radiation device
16 . . . I/O device
17 . . . control device
17a . . . current generation circuit
17b . . . current detection circuit
18 . . . thickness calculation device
18a . . . display circuit
18b . . . calculation circuit
18c . . . memory circuit
110 . . . ultrasonic wave transmission/reception device
111 . . . ultrasonic wave transmission device
112 . . . fixture device (support device)
119 . . . power generation device
210 . . . electromagnetic ultrasonic wave transmission/reception device
211 . . . connection device
211a . . . fixture
211b . . . thin wire
212 . . . selection device
218 . . . statistics calculation device
218a . . . display circuit
218b . . . arithmetic calculation and statistics processing circuit
219 . . . thickness distribution calculation device
219a . . . stereoscopic display circuit
219b . . . prediction circuit

The invention claimed is:

1. A thickness measurement apparatus comprising:
at least one ultrasonic wave transmission/reception device that receives and transmits an ultrasonic wave to/from a wall of a pipe to be inspected, covered with a heat insulation material;
at least one ultrasonic wave transmission device respectively inserted in a gap between the ultrasonic wave transmission/reception device and an outer surface of the pipe to be inspected, and configured by soft metal transmitting the ultrasonic wave;
a support device that supports the ultrasonic wave transmission/reception devices from the outer surface of the pipe to be inspected and contacts the ultrasonic wave transmission/reception devices with the pipe to be inspected in a circumferential direction and an axial direction of the pipe to be inspected;
a thickness calculation device that measures a propagation time of the ultrasonic wave received and transmitted by the ultrasonic wave transmission/reception device, and calculates a thickness of the pipe to be inspected;
a calibration board of which a thickness is predetermined, the calibration board is set in the gap between the electromagnetic ultrasonic wave transmission/reception device and the outer surface of the pipe when calibrating measurement accuracy of the at least one ultrasonic transmission/reception device and more than a thickness of a dead zone of the ultrasonic wave transmission/reception device; and
a calibration board adjustment device that moves the calibration board toward and away from the gap between the ultrasonic wave transmission/reception device and the outer surface of the pipe to be inspected.

2. The thickness measurement apparatus according to claim 1, wherein the support device is fixed to the heat insulation material.

3. The thickness measurement apparatus according to claim 1, wherein the ultrasonic wave transmission/reception device includes an electromagnetic acoustic transducer.

4. The thickness measurement apparatus according to claim 1, wherein the ultrasonic wave transmission/reception device includes an ultrasonic wave probe including an ultrasonic wave vibrator.

5. The thickness measurement apparatus according to claim 1, further comprising a heat radiation device of which one end is contacted with an outer surface of the heat insulation material and another end is contacted with the support device,
wherein the heat radiation device radiates a heat generated from the ultrasonic wave transmission/reception device through the support device.

6. The thickness measurement apparatus according to claim 1, further comprising a statistics processing device that measures the thickness of the pipe to be inspected by statistically calculating a plurality of measurement values obtained by the plurality of the ultrasonic wave transmission/reception devices.

7. The thickness measurement apparatus according to claim 1, a thickness distribution calculation device that calculates a thickness distribution based on a plurality of measurement values obtained by the plurality of the ultrasonic wave transmission/reception devices.

8. The thickness measurement apparatus according to claim 1, further comprising an electromotive force generation device that generates an electrical power from at least one of a heat or a vibration, of the pipe to be inspected and a light radiated from a lighting device therearound, and supplies the electrical power to at least the thickness calculation device.

9. A thickness measurement method, by using a plurality of apparatus including at least one ultrasonic wave transmission/reception device that receives and transmits an ultrasonic wave to/from a wall of a pipe to be inspected, covered with a heat insulation material, at least one ultrasonic wave transmission device respectively inserted in a gap between the ultrasonic wave transmission/reception device and an outer surface of the pipe to be inspected, and configured by soft metal transmitting the ultrasonic wave; a support device that supports the ultrasonic wave transmission/reception device from the outer surface of the pipe to be inspected and contacts the ultrasonic wave transmission/reception devices with the pipe to be inspected in a circumferential direction and an axial direction of the pipe to be inspected, and a thickness calculation device that measures a propagation time of the ultrasonic wave received and transmitted by the ultrasonic wave transmission/reception device, and calculates a thickness of the pipe to be inspected, a calibration board of which a thickness is predetermined and more than a thickness of a dead zone of the ultrasonic wave transmission/reception device, and a calibration board adjustment device that moves the calibration board toward and away from a gap between the ultrasonic wave transmission/reception device and the outer surface of the pipe to be inspected, comprising:

measuring the thickness of the pipe to be inspected by the ultrasonic wave transmission/reception device, the support device and the thickness calculation device;

setting the calibration board in the gap between the ultrasonic wave transmission/reception device and the pipe outer surface; and calibrating a setting for using the thickness measurement of the pipe to be inspected by measuring a thickness of the calibration board and comparing a measurement result of the thickness of the calibration board to the thickness of the calibration board which is predetermined, the calibration board is set in the gap between the electromagnetic ultrasonic wave transmission/reception device and the outer surface of the pipe when calibrating measurement accuracy of the at least one ultrasonic transmission/reception device.

* * * * *